United States Patent [19]

Nakamori et al.

[11] Patent Number: 4,601,983
[45] Date of Patent: Jul. 22, 1986

[54] CORYNEFORM BACTERIA CARRYING RECOMBINANT PLASMIDS AND THEIR USE IN THE FERMENTATIVE PRODUCTION OF L-THREONINE AND L-ISOLEUCINE

[75] Inventors: Shigeru Nakamori, Yokohama; Masaaki Ishida; Hiroshi Takagi, both of Kawasaki; Kiyoshi Miwa, Matsudo; Koichi Ito, Kawasaki; Konosuke Sano, Tokyo, all of Japan

[73] Assignee: Ajinomoto Co., Inc., Tokyo, Japan

[21] Appl. No.: 504,471

[22] Filed: Jun. 15, 1983

[51] Int. Cl.[4] .................. C12P 13/08; C12P 13/06; C12N 15/00; C12R 1/125
[52] U.S. Cl. .................... 435/115; 435/116; 435/172.3; 435/840; 435/843; 935/29; 935/60
[58] Field of Search .............. 435/115, 116, 172.1, 435/317, 172.3

[56] References Cited

U.S. PATENT DOCUMENTS 4,442,208  4/1984  Tsuchida et al. .................. 435/116
4,452,890  6/1984  Tsuchida et al. .................. 435/115

FOREIGN PATENT DOCUMENTS 0077548  4/1983  European Pat. Off. ............ 435/115

Primary Examiner—Lionel M. Shapiro
Assistant Examiner—R. Thomas Gallegos
Attorney, Agent, or Firm—Oblon, Fisher, Spivak, McClelland & Maier

[57] ABSTRACT

A genetic sequence coding for the production of a protein having the activity of homoserine dehydrogenase and having two Pst I cleavage sites in its DNA chain and a molecular weight of 2.24 Md, is incorporated into a vehicle capable of replication in Coryneform bacteria and used to produce L-threonine and L-isoleucine by fermentation.

2 Claims, 8 Drawing Figures

```
A  : AvaI
Bc : BcII
Bg : BgIII
E  : EcorRI
H  : HaeII
II : Hind II
```

CORYNEFORM BACTERIA CARRYING RECOMBINANT PLASMIDS AND THEIR USE IN THE FERMENTATIVE PRODUCTION OF L-THREONINE AND L-ISOLEUCINE

BACKGROUND OF THE INVENTION

1. Field of the Invention

The present invention relates to Coryneform bacteria containing plasmids made by recombinant DNA techniques carrying genetic information useful for the fermentative production of threonine and isoleucine.

2. Description of the Prior Art

It has been known in the prior art that in order to render a wild strain capable of producing L-threonine from carbohydrates it has been necessary to induce artificial mutants from the wild strain. There are many known L-threonine producing artificial mutants, most of which are resistant to α-amino-β-hydroxyvaleric acid (hereinafter referred to as AHV), and belonging to the genus Brevibacterium or Corynebacterium. These microorganisms produce L-threonine in a yield of from 10 to 20%. For example U.S. Pat. Nos. 3,582,471, 3,580,810 and Japanese Publication No. 47-34956 describe threonine producing mutants resistant to AHV and belonging to the genera Brevibacterium, Escherichia and Corynebacterium. Threonine production by mutants of the genera Brevibacterium and Corynebacterium is also described in Japanese Published Unexamined Patent Applications Nos. 51-54984, 53-101591, 54-32693, 54-35285, 54-35286, 54-35288, 54-37886 and 54-92692.

U.S. Pat. No. 4,278,765 and Japanese Published Unexamined Patent Applications Nos. 55-131397 and 56-15696 describe and discuss threonine producing Escherichia coli strains transformed with a recombinant plasmid DNA. Commonly assigned copending U.S. patent application Ser. No. 376,396 filed May 10, 1982 at the U.S. Patent and Trademark Office describes the production of L-threonine with Coryneform bacteria harboring a plasmid having inserted therein a chromosomal DNA fragment controlling resistance to AHV.

The situation with L-isoleucine is very similar to that of threonine. Examples of known L-isoleucine producing microorganisms include mutants of Serratia resistant to isoleucine hydroxamate (Japanese Published Examined Patent Application No. 30593/1977), mutants of Corynebacterium glutamicum requiring L-leucine for growth (Japanese Published Examined Patent Application No. 38995/1972), mutants of Brevibacterium and Corynebacterium resistant to AHV (Japanese Published Examined Patent Application No. 2880/1965), mutants of Brevibacterium resistant to AHV and requiring lysine for growth (Japanese Published Examined Patent Application No. 6237/1976), mutants of Brevibacterium resistant to AHV and O-methylthreonine (Japanese Published Examined Patent Application No. 21077/1976), mutants of Corynebacterium resistant to S-(2-aminoethyl)-cysteine (Japanese Published Examined Patent Application No. 4629/1977), mutants of Escherichia resistant to 2-amino-3-methylthiobutyric acid (Japanese Published Unexamined Patent Application No. 69881/1978), and mutants of Brevibacterium resistant to AHV and trichloroalanine (Japanese Published Unexamined Patent Application No. 35287/1979).

The prior art has also described Escherichia coli strains transformed with a recombinant plasmid DNA, which strains have increased productivity of amino acids (See, for example, U.S. Pat. No. 4,278,765). It has generally been difficult, however, to construct commercially useful threonine (Thr) or isoleucine (Ile) producers of *Escherichia coli* by gene splicing techniques, because the original Escherichia strains do not express high productivity for threonine and isoleucine, and recombinant strains derived from such Escherichia strains do not produce high amounts of either amino acid.

On the other hand, there are many strains in the genera of Brevibacterium and Corynebacterium which produce high amounts of L-threonine and L-isoleucine. Strains of Corynebacterium and Brevibacterium may thus be suitable as original strains for construction of L-threonine and L-isoleucine producers by gene recombination techniques.

Although the presence of plasmids in strains of Brevibacterium and Corynebacterium having detectable phenotypic markers has not been known for a long time (but see, e.g., Published European Patent Application No. 003391), recent work has demonstrated the feasibility of preparing Coryneform bacteria harboring plasmids controlling the production of threonine or isoleucine (See the aforementioned commonly assigned, Ser. No. 376,396, copending at the U.S. Patent and Trademark Office filed May 10, 1982 (Thr), and commonly assigned copending Ser. No. 392,145, filed June 25, 1982 at the U.S. Patent and Trademark Office (Ile)). In addition, commonly assigned copending U.S. patent application Ser. No. 386,980 filed on June 10, 1982 at the U.S. Patent and Trademark Office, describes composite plasmids capable of propagating in Coryneform glutamic acid producing bacteria. (All of these patent applications are herein fully incorporated by reference).

A brief schematic representation of the isoleucine and threonine biosynthetic pathway is as follows:

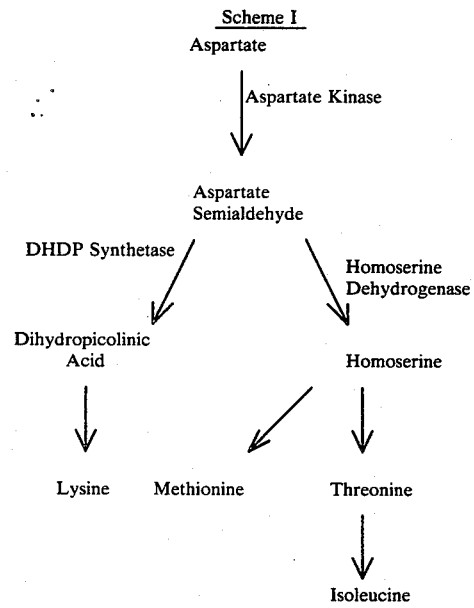

Scheme I

In Scheme I is also shown part of the lysine biosynthetic pathway. The first branch of the pathway leading to threonine and isoleucine can be found at the junction of aspartate semialdehyde. The enzyme leading to these two amino acids is homoserine dehydrogenase (hereinafter "HDase"), while the enzyme leading to lysine is dihydrodipicolinate synthetase, ("DHDP synthetase").

The relationship between homoserine dehydrogenase activity and resistance to AHV in mutants of Corynebacteria is disclosed in Shiio et al Journal of Biochemistry 68: 859 (1970), Nakamori et al Agric. Biol. Chem. 37: 653 (1973), and Tosaka et al ibid 43: 265 (1979).

It should also be noted here that, recently, Escherichia coli strains were described which carry hybrid plasmids containing several genes of the lysine biosynthetic pathway. An overproducer of lysine (TOC R 21) was transformed, and the synthesis of lysine was studied in different strains (See, for example, LeReverend et al, European Journal of Applied Microbiology and Biotechnology, 15: 227-231 (1982), as well as published French Patent Application No. 2511032 (Application No. 81/15385) published Feb. 11, 1983). It appears from these publications that only plasmids containing the dapA gene (encoding DHDP synthetase) lead to an increase in lysine production; this reaction is the limiting biosynthetic step in lysine overproducers (having mutations altering the aspartokinase reaction). The authors suggest that such a method of gene amplification could be used to improve strains which overproduce metabolites. There is no suggestion in these publications, however, to expand this work to Coryneform bacteria or to any other products than lysine.

A need therefore still exist for improved and efficient methods for the fermentative production of L-threonine and L-isoleucine in Coryneform bacteria.

SUMMARY OF THE INVENTION

The inventors have discovered that when the genetic information coding for homoserine dehydrogenase (HDase) is combined into an appropriate vehicle capable of replication in Coryneform bacteria, and the resulting hybrid vehicle carrying said genetic information is replicated in an appropriate Coryneform bacterium host or recipient, the transformed Coryneform microorganism is an excellent producer of L-threonine or L-isoleucine. This invention is of particular interest since many strains of Brevibacterium and Corynebacterium genera within the Coryneform type producing high amounts of L-threonine and L-isoleucine can be utilized as hosts.

The invention thus relates to a process for the fermentative production of L-threonine and L-isoleucine, and to the various genetic and microbiological elements involved in said process. For example, the invention relates to the isolated form of the gene for homoserine dehydrogenase, to various vehicles containing said gene, which vehicles are replicable in Coryneform bacteria, to various microbes of the Coryneform type containing such vehicles, and to various fermentation processes for the production of L-threonine and L-isoleucine.

DESCRIPTION OF THE PREFERRED EMBODIMENTS

Figure 1:
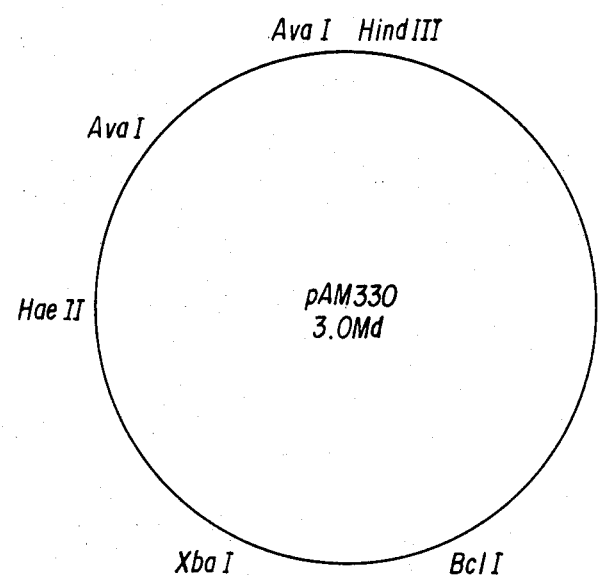
FIG. 1 shows a restriction map of plasmid pAM 330.

The biosynthetic pathway for the production of lysine, threonine and isoleucine is shown in the "Description of the Prior Art". The scheme demonstrates the presence of homoserine dehydrogenase enzyme in one of the branching points between the pathways leading towards lysine and the pathways leading to L-threonine and L-isoleucine. DNA containing sufficient genetic information to code for HDase is obtained from an appropriate DNA donor. The donor may be one which is either mutated in HDase, or which is wild in HDase. Preferably, the donor is a Coryneform bacterium, most preferably Brevibacterium lactofermentum. The most preferred donor has HDase insensitive to feedback inhibition by L-threonine. Such donor is usually resistant to AHV. The genetic information coding for HDase can be obtained by partial digestion of DNA from the donor, introduction of the genetic sequence into an appropriate plasmid, transformation of an HDase deficient Coryneform bacteria and then a homoserine auxotroph (HDase−) with the resulting mixture of recombinant DNAs, and isolation of transformants which do not require homoserine.

In particular, the HDase genetic information-containing sequence may be obtained from Brevibacterium lactofermentum AJ11188 (deposited at the FERM with deposit number FERMP-4190), wherein homoserine dehydrogenase is resistant to feedback inhibition by L-threonine. The genetic information comprising the HDase gene can be found in a DNA fragment having a molecular weight of 2.24 megadaltons, having two Pst I restriction endonuclease sites, and being flanked by two Pst I sites. This DNA fragment thus has three portions, and the sizes of these three portions (flanked and divided by two Pst I sites) are 0.7 Md, 0.44 Md and 1.10 Md.

The recipients or hosts useful for the transformation are the so called Coryneform bacteria. These are aerobic, Gram positive rods, non acid fast, and are described in Bergey's Manual of Determinative Bacteriology 8th Edition, page 599 (1974). Examples of specimens of wild strains of Coryneform bacteria useful as hosts in the invention are as follows:

Brevibacterium divaricatum ATCC 14020,
Brevibacterium saccarolyticum ATCC 14066,
Brevibacterium immariophilum ATCC 14068,
Brevibacterium lactofermentum ATCC 13869,
Brevibacterium roseum ATCC 13825,
Brevibacterium flavum ATCC 13826,
Brevibacterium thiogenitalis ATCC 19240,
Corynebacterium acetoacidophilum ATCC 13870,
Corynebacterium acetoglutamicum ATCC 15806,
Corynebacterium callunae ATCC 15991,
Corynebacterium glutamicum ATCC 13032, 13060,
Corynebacterium lilium ATCC 15990,
Corynebacterium melassecola ATCC 17965, and others.

A preferred result may be obtained when the Coryneform bacteria are mutated in a known manner to a reduced restriction enzyme activity prior to using them as the hosts.

When the Coryneform bacteria are transformed with vehicles carrying the homoserine dehydrogenase insert they then express the genetic information possessed by the foreign gene.

Of particular interest are hosts which are either auxotrophs for homoserine dehydrogenase or prototrophs therefor. In the latter case, the host itself produces L-threonine and L-isoleucine. Insertion of a gene coding for homoserine dehydrogenase, especially in a multicopy plasmid, greatly increases the number of gene copies for this enzyme, and greatly increases the production of final amino acids. In fact, the highest concentrations of L-threonine and L-isoleucine may be obtained by the use of multicopy plasmids carrying the HDase gene in a HDase prototrophic (HDase+) host. Auxotrophs for HDase are usually used as the hosts for selection and isolation of the vehicles carrying the HDase gene. It is then convenient to use the thus isolated vehicle for the transformation of prototrophs for HDase.

Also of interest is the use of either aspartokinase wild hosts, or hosts which have been mutated by altering the aspartokinase reaction. In hosts wherein the aspartokinase reaction has been mutated so that the hosts overproduce threonine and/or isoleucine, the aspartokinase reaction is no longer rate limiting. The maximum effect can thus be obtained by utilizing such a mutated host.

Further, non AHV resistant hosts can be utilized for the transformation. Auxotrophs for L-methionine, L-lysine and/or L-leucine are preferred hosts. Most preferred hosts are resistant to AHV and have HDase tolerant to feedback inhibition by L-threonine.

Any replicable vehicle, capable of replication in Coryneform bacteria can be utilized to carry the HDase gene into, and be used for the transformation of the hosts. Vehicles such as plasmids, phages or other vectors can be utilized. Of particular importance are the composite plasmids disclosed in copending Ser. No. 386,980, filed at the U.S. Patent and Trademark Office June 10, 1982. These plasmids comprise (A) a drive unit region derived from a plasmid (a) capable of propagating in Coryneform glutamic acid producing bacteria, and (B) a gene fragment or fragments derived from a plasmid (b) capable of propagating in *Escherichia coli* or *Bacillus subtilis,* and having at least a region to express resistance to a drug. When the gene fragment additionally carries a drive unit region of plasmid (b), the composite plasmid becomes capable of propagating in *Escherichia coli* or *Bacillus subtilis,* and thus it can be screened or amplified in *Escherichia coli* or *Bacillus subtilis.*

By the terms "resistance to a drug" is meant to imply resistance to a drug such as an antibiotic which inhibits the growth of a host cell. Examples of such antibiotics are penicillin, kanamycin, chloramphenicol, erythromycin, actinomycin, and the like.

Figure 2:
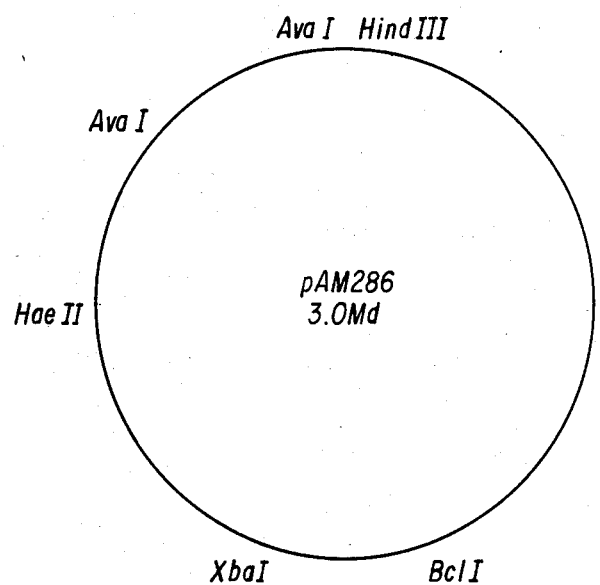
FIG. 2 shows a restriction map of plasmid pAM 286.
Figure 3:
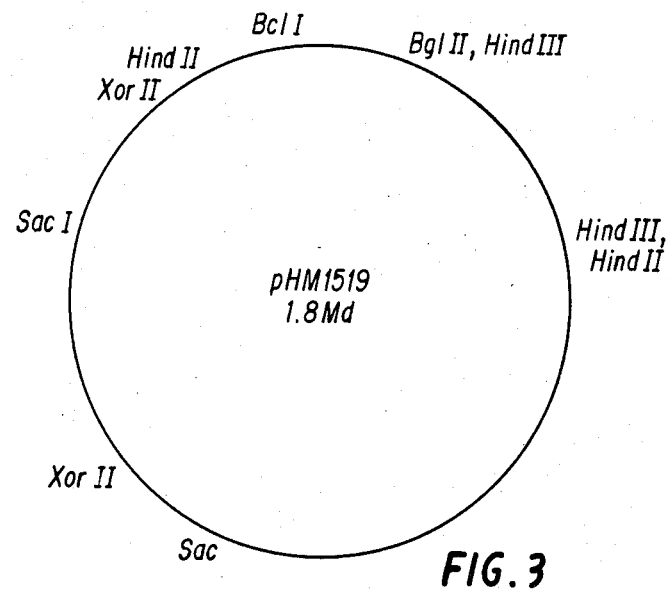
FIG. 3 shows a restriction map of plasmid pHM 1519.

Specimens of multicopy plasmids (a) capable of propagating in Coryneform bacteria are shown in application Ser. No. 386,980, and include pAM 330, separated from *Brevibacterium lactofermentum* ATCC 13869, having a molecular weight of 3.0 megadalton (restriction map in FIG. 1), pAM 286 separated from *Corynebacterium glutamicum* FERM-B 5485, having a molecular weight of 3.0 megadalton (restriction map in FIG. 2), and pHM 1519 separated from *Brevibacterium glutamicum* ATCC 13058, having a molecular weight of 1.8 megadalton (restriction map in FIG. 3).

Plasmids (b) capable of propagating in *Escherichia coli* are multicopy plasmids and have genetic information of resistance to a drug. They are, for example, pAC 105, pBR 322, pBR 324, pBR 325, and the like. Plasmids (b) capable of propagating in *Bacillus subtilis* and having genetic information of resistance to a drug are preferably multicopy, and include pT 127, pC 194, pC 221, pC 223, pUB 110 and the like.

In order to construct the composite plasmid from the plasmids (a) and (b), conventional methods can be employed such as digestion with restriction enzymes, and ligation with ligases.

After the ligation reaction, the desired composite plasmids are screened by isolating plasmids which can propagate in Coryneform bacteria, and can transform the Coryneform bacteria into drug resistance. A composite plasmid having a drive unit region derived from plasmid (a) and another drive unit region derived from plasmid (b), and the drug resistance genes of plasmid (b) can be found among plasmids which can propagate in Coryneform bacteria and *Escherichia coli* or *Bacillus subtilis,* and which can tranform the (1) Coryneform bacteria or (2) *Escherichia coli* (in the case where a plasmid was used capable of propagating in *Escherichia coli*), or *Bacillus subtilis* (in case where a plasmid was capable of propagating in *Bacillus subtilis*), and which are drug resistant.

Figure 4:
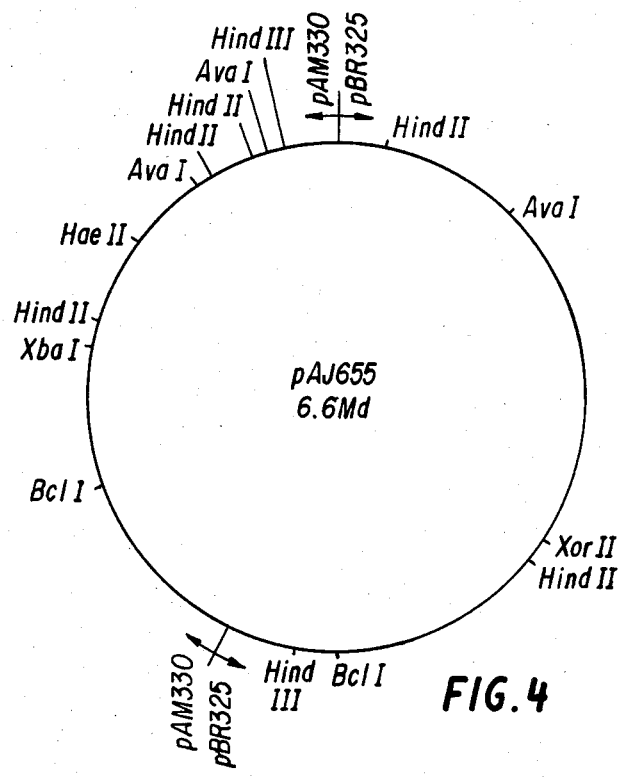
FIG. 4 shows a restriction map of composite plasmid pAJ 655.
Figure 5:
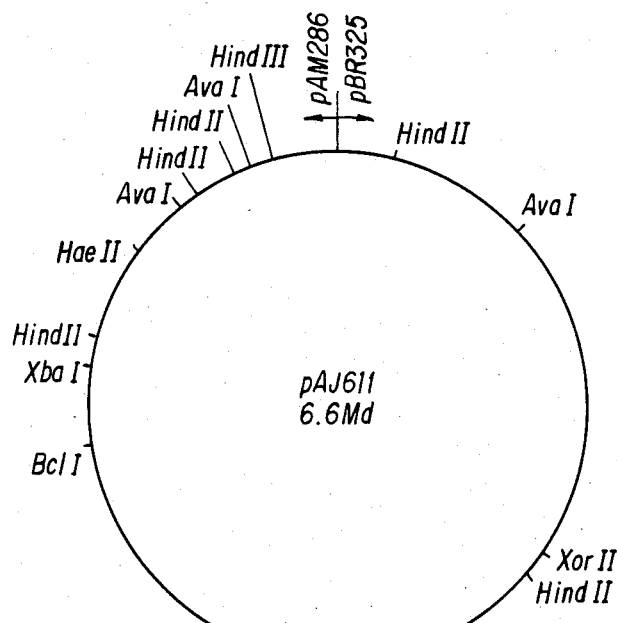
FIG. 5 shows a restriction map of composite plasmid pAJ 611.
Figure 6:
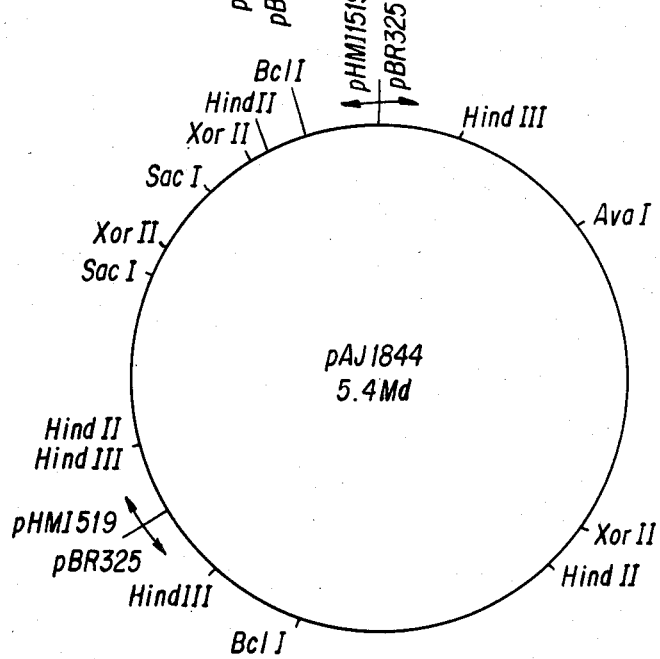
FIG. 6 shows a restriction map of composite plasmid pAJ 1844.
Figure 7:
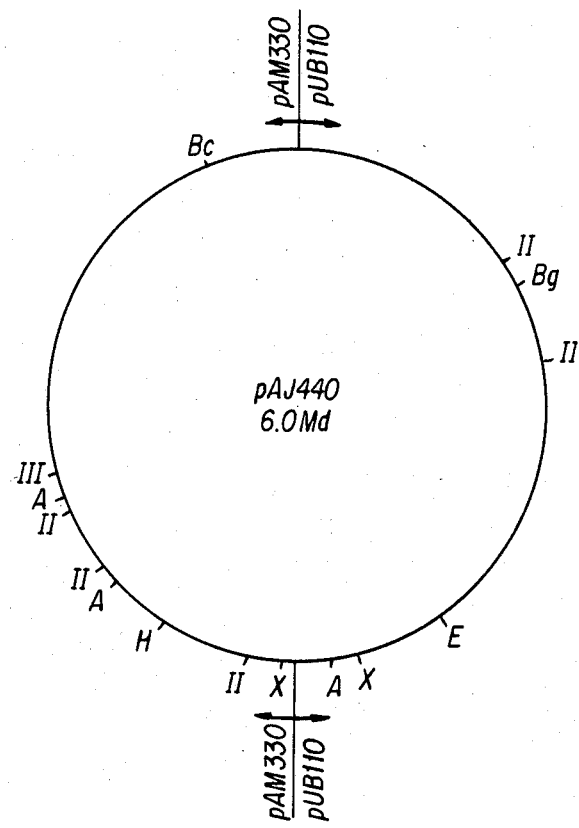
FIG. 7 shows a restriction map of composite plasmid pAJ 440.
Figure 8:
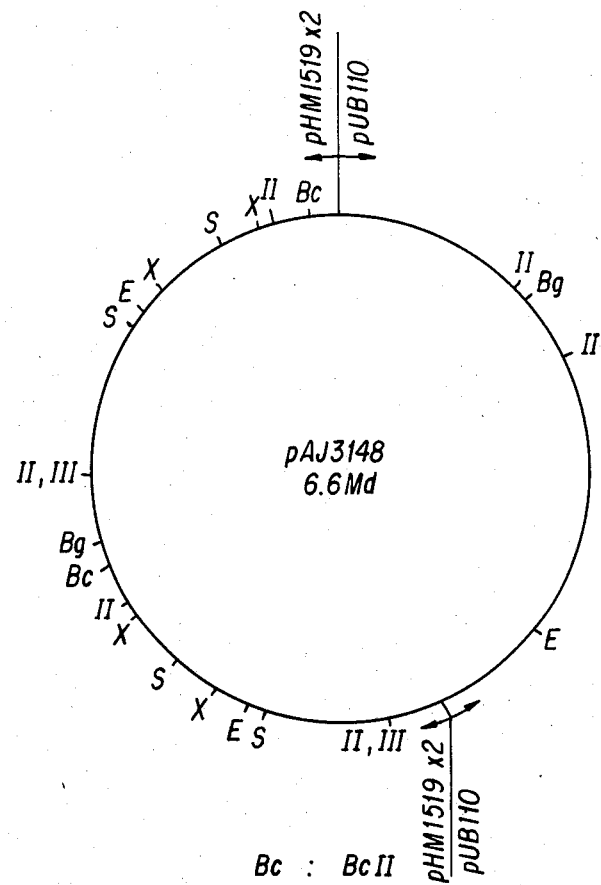
FIG. 8 shows a restriction map of composite plasmid pAJ 3148.

Among the examples of composite plasmids useful in the present invention are those present in hosts deposited at appropriate international depository authorities as follows:

| | |
|---|---|
| pAJ 655: | *Escherichia coli* AJ11882, FERM-BP 136, (FERM-P6517); |
| | *Corynebacterium glutamicum* SR 8201 ATCC 39135 (restriction map in FIG. 4); |
| pAJ 611: | *Escherichia coli* AJ 11884, FERM-BP 138 (FERM-P6519) (restriction map in FIG. 5); |
| pAJ 1844: | *Escherichia coli* AJ 11883, FERM-BP 137 (FERM-P 8518); |
| | *Corynebacterium glutamicum* ATCC 39136 (restriction map in FIG. 6); |
| pAJ 440: | *Bacillus subtilis* AJ 11901, FERM-BP 140 (restriction map in FIG. 7); |
| pAJ 3148: | *Corynebacterium glutamicum* SR 8203 ATCC 39137 (restriction map in FIG. 8). |

The composite plasmids can be obtained from the cells of the microorganisms on deposit, by lysing the cells previously harvested at late exponential growth phase with hysozyme and SDS, adding polyethylene glycol to the supernatant obtained from the lysate by centrifugation at 30,000 xg, and purifying the precipitated DNA by fractionation using cesium chloride-ethidium bromide equilibrium density gradient centrifugation. The composite plasmids can also be expelled to obtain host strains without injury thereto from the deposited microorganisms by spontaneous loss or "curing" (Bacteriological Reviews, 36: 361–405 (1972)).

Insertion of the HDase gene into one of the appropriate replication vehicles can be done by restriction of the replication vehicle with appropriate endonuclease enzymes, and ligation of the appropriate gene sequence thereinto, as is well known in the art.

The incorporation of the vehicle carrying the HDase gene into the hosts of Coryneform bacteria can be done by treating the cells of the DNA recipient with calcium chloride to increase the permeability of DNA (as is reported regarding *E. coli* K-12 by Mandell, M et al, Journal of Molecular Biology, 53: 159 (1970)), or by incorporating at a specific stage of growth when cells become capable of incorporating DNA (as is reported for Bacillus subtilis by Duncan, C. H. et al, Gene, 153 (1977)). The plasmids can also be incorporated into the recipients by forming protoplasts or spheroplasts of the DNA recipients which easily incorporate plasmid DNA, as is known for Bacillus subtilis, Actinomycetes and yeast, and reported by Chang, S. et al, Molec. Gen. Genet. 168: 111 (1979), Bibb et al, Nature, 274: 398 (1978), Hinnen, A. et al, PNAS USA, 75: 1929 (1978)).

Since the composite plasmids transform the Coryneform bacteria into drug resistant bacteria, the transformants which contain the plasmids inserted with the HDase gene can be easily identified by testing their resistance to the drug. When vehicles having no genetic markers are used for the preparation of the recombinant DNA, auxotrophs for HDase are preferred as the hosts, since transformants carrying the vehicle inserted with the HDase can be easily distinguished from the host cells by testing their homoserine requirement for growth.

The HDase gene inserted in the composite plasmid can be transferred easily into another vehicle by conventional methods, if necessary.

The methods of culturing the L-threonine and L-isoleucine producing strains thus obtained are conventional, and are similar to the methods for the cultivation of known threonine and isoleucine producing microorganisms. The culture medium employed can be a conventional medium containing carbon sources, nitrogen sources, and organic ions and, when required, minor organic nutrients such as vitamins and amino acids. Examples of suitable carbon sources include glucose, sucrose, lactose, starch hydrolysate, and molasses. Gaseous ammonia, aqueous ammonia, ammonia salts and other nitrogen-containing materials can be used as the nitrogen source.

Cultivation of the transformed organisms containing the vehicle carrying the HDase gene is conducted under aerobic conditions in which the pH and the temperature of the medium are adjusted to a suitable level, and continued until the formation of L-isoleucine and L-threonine ceases.

The amino acids which accumulate in the culture medium can be recovered by conventional procedures.

By the methods of the present invention, L-isoleucine and L-threonine can be produced in higher yields than has been achieved in previously known methods using artificial mutants of Brevibacterium and Corynebacterium.

Having generally described this invention, a further understanding can be obtained by reference to certain specific examples which are provided herein for purposes of illustration only and are not intended to be limiting unless otherwise specified.

EXAMPLE 1

(1) An L-threonine producing strain Brevibacterium lactofermentum AJ 11188 (FERM-P 4190) in which homoserine dehydrogenase is resistant to feedback inhibition by L-threonine (resistant to AHV (α-amino-α-hydroxy valeric acid) [Tosaka, O. et al, Agric. Biol. Chem., 43: 265 (1979)] was used as the DNA-donor.

AJ 11188 was cultured in 1 l of CMG medium (peptone 10 g, yeast extract 10 g, NaCl 5 g, glucose 5 g, distilled water 1,000 ml) (pH 7.0 (with NaOH)) at 30° C. for 10 hr, and cells were harvested by centrifugation at exponential growth phase. From the cells, about 3.6 mg of DNA was extracted by the conventional phenol method.

(2) Plasmid pAJ1844 is a composite plasmid constructed from plasmids pAM 1519 and pBR325. Restriction maps of plasmids pAM1519 and pAJ1844 are shown in U.S. application Ser. No. 386,980.

Plasmid pAJ1844 was prepared as follows:

Cells of E. coli AJ11883 possessing PAJ1844 were harvested at an exponential growth phase by centrifugation, and lysed by lysozyme and SDS. From the supernatant of the lysate, about 80 μg of the DNA of pAJ1844 was obtained by ethanol precipitation.

(3) A sample of 4.0 μg of the chromosomal DNA was partially digested with 0.124 units of restriction enzyme Pst I (purchased from Boehringer Mannheim) at 30° C. for 10 min. The plasmid pAJ1844 DNA obtained in (2) (2.0 μg) was also digested with 5.0 units of Pst I at 30° C. for 120 min. The digested DNAs were mixed, and ligated with 0.2 units of T4 phage DNA ligase at 22° C. for 15 hr, obtaining a mixture of recombinant DNAs.

(4) Brevibacterium lactofermentum AJ 12019 (NRRL B-15346), a homoserine auxotroph, was cultured in 5 ml of CMG medium, 0.6 units/ml of penicillin G was added to the culture medium at an early exponential growth phase, and the cultivation was continued further for 1.5 hours. Cells were collected by centrifugation and washed with 0.5 ml of SMMP medium composed of 0.5 M sucrose, 20 mM maleic cid, 20 mM $MgCl_2$, and 3.5% "Pennassay broth" (Difco) (pH 6.5). Protoplasts were prepared from these cells by treatment with 10 mg/ml lysozyme in SMMP medium at 30° C. for 20 hours (followed by centrifugation at 6,000 xg for 10 minutes), washed with SMMP medium and resuspended in 0.5 ml SMMP.

Protoplasts thus obtained were mixed with 10 μl of the recombinant DNAs obtained above and added with final 30% polyethyleneglycol to the mixture, and kept at a room temperature for 2 minutes in order to introduce the DNA into the protoplasts. After having been washed in 1 ml of SMMP medium, the protoplasts were resuspended in 1 ml of SMMP medium, and cultured at 30° C. for 3 hours.

The resulting culture liquid was spread onto a "protoplast regeneration medium" of pH 7.0, which contained, per one liter of distilled water 12 g Tris(hydroxymethyl)aminomethane, 0.5 g KCl, 10 g glucose, 8.1 g $MgCl_2.6H_2O$, 2.2 g $CaCl_2.2H_2O$, 4 g peptone, 4 g yeast extract, 1 g "Casamino acid" (Difco), 0.2 g $K_2HPO_4$, 135 g Na-succinate, 18 g agar and 3 μg/ml chloramphenicol. Among five colonies which appeared after 10 days of the cultivation at 30° C., a transformant, AJ 12020 (FERM BP-269) was selected for further examination.

The recipient strain AJ 12019 required L-homoserine for its growth, while the transformant AJ 12020, did not require the same. The recipient could not grow on CMG medium supplemented with 3 μg/ml of chloramphenicol, while the transformant could grow on CMG medium with 3 or 10 μg/ml of chloramphenicol. The recipient had no plasmid, but the transformant had a plasmid, named pAJ 210.

The DNA of the plasmid pAJ 210, was isolated from the cell lysate of AJ 12020 by the following method:

Cells of AJ 12020 were obtained after cultivation in CMG medium, lysed by a conventional method (Tanaka et al, J. Bacteriol., 121, 354 (1979)), and the lysate was applied to agarose gel and electrophoresed (Sharp et al, *Biochemistry* 12, 3055 (1973)), whereby the molecular weight of the plasmid was determined as 7.64 Md.

These facts indicate that a fragment of 2.24 Md of chromosomal DNA was cloned into the Pst I site of plasmid pAJ 1844. This 2.24 Md fragment was further digested with Pst I, and three fragments of 1.1, 0.7 and 0.44 Md were obtained by the digestion, showing that the 2.24 Md fragment has two Pst I sites.

(6) L-Threonine Production by the Transformant

Table 1 shows the experimental result of the fermentative production of L-threonine by AJ 12020.

The fermentation medium PM-1 contained per 1 liter of distilled water, 100 g glucose, 30 g $(NH_4)_2SO_4$, 1 g $KH_2PO_4$, 0.4 g $MgSO_4.7H_2O$, [Aji-eki] 10 ml, hydrolyzed soybean protein [Mieki], 200 μg biotin, 300 μg thiamine HCl, 50 g $CaCO_3$, 10 mg $FeSO_4.7H_2O$, 10 mg $MnSO_4.5H_2O$. The pH of the medium was adjusted to 7.0 with KOH. Twenty ml batches of the medium were put into 500 ml flasks, inoculated with AJ 12020, and shaken at 30° C. for 7 hr. Amounts of L-threonine produced were determined by microbioassay with *Lenconostoc mesenteroides*. The recipient strain AJ 12019 was cultured by the same method except 800 mg L-homoserine was added to the medium.

TABLE 1

| Strain | L-threonine produced (g/l) |
|---|---|
| AJ 12020 | 1.10 |
| AJ 12019 | 0.001 |

EXAMPLE 2

*Brevibacterium lactofermentum* AJ 11188 (HDase+) was transformed with plasmid pAJ 210 DNA obtained in Example 1-4, and chloramphenicol resistant transformant AJ12021 (FERM-BP 270) was selected by the same method as in Example 1-4.

These transformants were confirmed to harbour plasmids of the same molecular weight of pAJ 210.

The transformant was cultured to produce L-threonine by the same method as in Example 1-5 except 300 mg L-isoleucine and 300 mg L-leucine were added to the culture medium (PM-1)

Table 2 shows the result of fermentative production of L-threonine by AJ 12021.

TABLE 2

| Strain | L-threonine produced (g/l) |
|---|---|
| AJ 12021 | 17.80 |
| AJ 11188 | 10.90 |

Homoserine dehydrogenase activity of the transformant AJ 12021 was measured by the manner as described in Miyajima et al (J. Biochemistry, 68, 311 (1970).

HDase activity of AJ 12021 was about twice as high as that of AJ 11188.

EXAMPLE 3

*Corynebacterium glutamicum* ATCC 13287 (a homoserine auxotrophic mutant) was transformed with plasmid pAJ 210 DNA obtained in Example 1-4, and a chloramphenicol resistant, prototrophic transformant SR8301 (NRRL B-15348) was selected by the same method as in Example 1-4. The transformant was cultured, and the amount of L-threonine produced was determined by paper chromatography followed by ninhydrin reaction.

Table 3 shows the result of the production of L-threonine by SR8301. The recipient strain ATCC 13287 was cultured by adding 800 mg/l of L-homoserine.

TABLE 3

| Strain | L-threonine produced (g/l) |
|---|---|
| SR 8301 (transformant) | 1.5 |
| ATCC 13287 (Recipient) | 0.0 |

EXAMPLE 4

Transformant *Brevibacterium lactofermentum* AJ 12020, obtained in Example 1-4 produced L-isoleucine. Table 4 shows the analytical results of the culture broth obtained in Example 1-6.

The amount of L-isoleucine produced was determined by microbioassay with *Leuconostoc mesenteroides*.

TABLE 4

| Strain | L-isoleucine produced (g/l) |
|---|---|
| AJ 12020 (TF) | 3.10 |
| AJ 12019 (Rec) | 0.01 |
| AJ 11188 (Donor) | 0.00 |

EXAMPLE 5

*Brevibacterium lactofermentum* AJ12028 (FERM-BP 272) is an L-isoleucine producer, selected as S-(2-aminoethyl)-cysteine, AHV and β-hydroxyleucine-resistant and leucine auxotroph. This strain was transformed with plasmid pAJ 210 DNA obtained in Example 1-4, and a chloramphenicol resistant transformant AJ 12027 (FERM-BP 271) was selected by the same method as in Example 1-4.

The transformant was cultured by the manner as in Example 1"5 except that 300 mg/ml of L-leucine was added to the culture medium and the amount of L-isoleucine produced was determined by the manner as in Example 4.

TABLE 5

| Strain | L-isoleucine produced (g/l) |
|---|---|
| AJ 12027 | 10.20 |
| AJ 12028 | 7.60 |
| AJ 11188 | 0.00 |

EXAMPLE 6

Table 6 shows the fermentative production of L-isoleucine by Corynebacterium glutamicum SR 8301 (NRRL 15348), obtained in Example 3, and ATCC 13287, as the recipient strain. The amount of L-isoleucine was determined by paper chromatography.

TABLE 6

| Strain | L-isoleucine produced (g/l) |
|---|---|
| NRRL 15348 | 1.0 |
| ATCC 13287 | 0.0 |

Having now fully described this invention, it will be understood by those of skill in the art that the same can be performed within a wide and equivalent range of parameters, hosts, DNA donors, transformants, methods of fermentation and the like, without affecting the spirit or scope of the invention.

What is claimed as new and intended to be covered by Letters Patent of the United States is:

1. A method of producing L-isoleucine by fermentation which comprises:
    (a) culturing in an appropriate medium a bacterium comprising a Coryneform host containing a vehicle capable of replication in a Coryneform bacterium containing genetic information coding for the production of a protein having the activity of homoserine dehydrogenase, wherein said host is resistant to α-amino-β-hydroxyvaleric acid, and
    (b) recovering L-isoleucine from said medium; and wherein said Coryneform bacterium is selected from the group consisting of those having the identifying characteristics of FERM BP-270 and FERM BP-271.

2. A method of producing L-threonine by fermentation which comprises:
    (a) culturing in an appropriate medium a bacterium comprising a Coryneform host containing a vehicle capable of replication in a Coryneform bacterium containing genetic information coding for the production of a protein having the activity of homoserine dehydrogenase, wherein said host is resistant to α-amino-β-hydroxyvaleric acid, and
    (b) recovering L-threonine from said medium; and wherein said Coryneform bacterium is selected from the group consisting of those having the identifying characteristics of FERM BP-270 and FERM BP-271.

* * * * *